(12) United States Patent
Smith et al.

(10) Patent No.: US 11,786,332 B2
(45) Date of Patent: Oct. 17, 2023

(54) SINGLE X-RAY MARKER

(71) Applicant: XRAYDEPOT LLC, Stafford, VA (US)

(72) Inventors: Van N. Smith, Stafford, VA (US); Kasey Smith, Stafford, VA (US)

(73) Assignee: XRAYDEPOT LLC, Stafford, VA (US)

( * ) Notice: Subject to any disclaimer, the term of this patent is extended or adjusted under 35 U.S.C. 154(b) by 420 days.

(21) Appl. No.: 15/963,403

(22) Filed: Apr. 26, 2018

(65) Prior Publication Data
US 2018/0333220 A1 Nov. 22, 2018

Related U.S. Application Data

(63) Continuation-in-part of application No. 29/604,451, filed on May 17, 2017, now Pat. No. Des. 841,815, and a continuation-in-part of application No. 29/604,443, filed on May 17, 2017, now Pat. No. Des. 824,519, and a continuation-in-part of application No. 29/604,469, filed on May 17, 2017, now Pat. No. Des. 827,828.

(51) Int. Cl.
*A61B 90/00* (2016.01)

(52) U.S. Cl.
CPC ...... *A61B 90/39* (2016.02); *A61B 2090/3941* (2016.02); *A61B 2090/3966* (2016.02)

(58) Field of Classification Search
CPC . G03B 42/04; A61B 90/39; A61B 2090/3941; A61B 2090/3966
See application file for complete search history.

(56) References Cited

U.S. PATENT DOCUMENTS

| 4,058,733 A | 11/1977 | Stembel |
| 4,429,412 A * | 1/1984 | Pierce ............... G03B 42/047 378/165 |
| 4,698,836 A * | 10/1987 | Minasian ........... G03B 42/047 378/162 |

(Continued)

FOREIGN PATENT DOCUMENTS

| CH | 680403 A5 * | 8/1992 | ............ G09F 13/20 |
| GB | 2440587 | 8/2010 | |
| WO | WO2016134093 A1 * | 8/2016 | ............... G06K 9/20 |

OTHER PUBLICATIONS

Srivastava 2013 Hinge Modelling extracted from YouTube presentation 3 extracted pages; (Year: 2013).*

(Continued)

*Primary Examiner* — Christopher Koharski
*Assistant Examiner* — Patrick M Mehl
(74) *Attorney, Agent, or Firm* — Charisse Hines Law

(57) ABSTRACT

A single marker for use in recording either of two different characters, an "R" or an "L," on an x-ray image, corresponding to the "left" or "right" side exposure area of the anatomical part(s) of a patient. The marker consists of four embodiments, a base marker, a swivel marker, a hinge marker, or a slider marker, which selectively indicate either the "R" or "L" exposure area of the patient. In addition, the marker also glows in the dark to facilitate usage in poorly lit areas and includes a radiopaque frame within its base to help the x-ray technician confirm that the technician is not viewing image artifacts.

13 Claims, 9 Drawing Sheets

(56) References Cited

U.S. PATENT DOCUMENTS

| | | | | |
|---|---|---|---|---|
| 5,356,209 A | * | 10/1994 | Hill | A63C 17/06 |
| | | | | 280/11.223 |
| 5,592,527 A | * | 1/1997 | Ray | G03B 42/047 |
| | | | | 378/162 |
| 5,640,438 A | | 6/1997 | Talluto et al. | |
| 2016/0331155 A1 | * | 11/2016 | Atkins | F16M 11/10 |
| 2017/0095314 A1 | * | 4/2017 | Baldwin | A61M 25/09041 |
| 2017/0211248 A1 | * | 7/2017 | Starts | E01F 13/028 |

OTHER PUBLICATIONS

Etsy.com internet address https://www.etsy.com/listing/194330393/1-set-glow-in-the-dark-x-ray-markers with comments of Buyers dated on Apr. 12, 2017, Mar. 14, 2017 and Mar. 8, 2016; 57 pages (Year: 2017).*

Chadwick et al. 2001 MD&DI Jun. 2001 Radiolucent Structural Materials for Medical Applications (Year: 2001).*

* cited by examiner

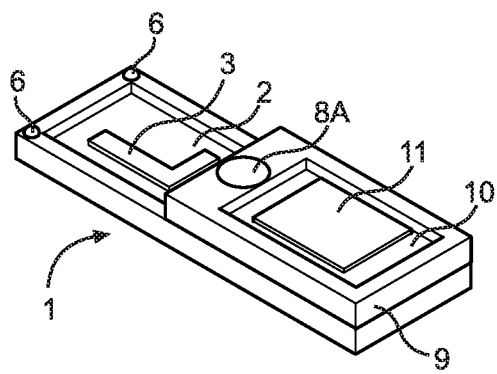
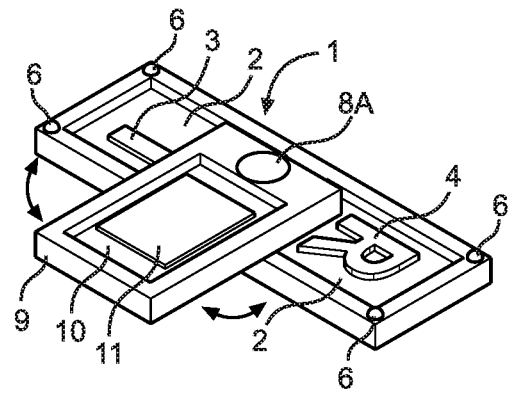
FIG. 6                FIG. 7
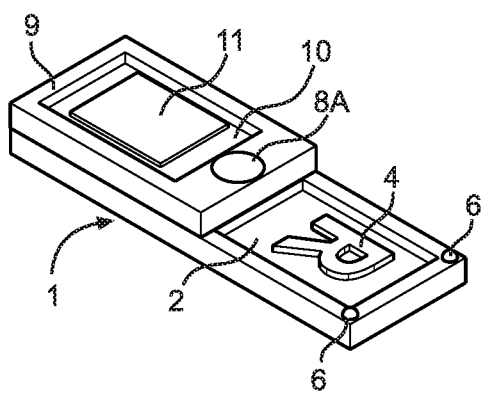
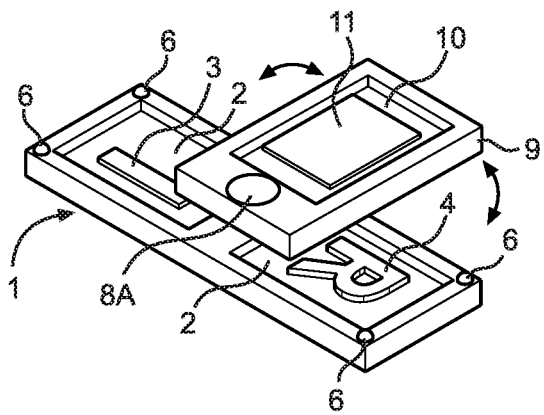
FIG. 8                FIG. 9

SINGLE X-RAY MARKER

CROSS-REFERENCE TO RELATED APPLICATIONS

This application is a continuation-in-part of U.S. Patent Application No. 29/604,443, filed May 17, 2017, a continuation-in-part of U.S. Patent Application No. 29/604,451, filed May 17, 2017, and a continuation-in-part of U.S. Patent Application No. 29/604,469 filed May 17, 2017.

BACKGROUND OF THE INVENTION

I. Field of the Invention

The present invention relates generally to medical instruments and more specifically it relates to x-ray imaging identification markers used to identify the left or right side of the anatomical part(s) of a patient, and other indicia taken during x-rays, such as the healthcare facility or the initials of an x-ray technician's name. Particularly, this invention relates to a single identification marker capable of marking either an "R" or an "L" to indicate the anatomical part(s) of a patient that glows in the dark and provides a radiopaque frame around its base to distinguish it from image artifacts on the x-ray image.

Specifically, this invention involves four embodiments of a single x-ray marker: a base marker, a swivel marker, a slider marker, and a hinge marker, capable of indicating either the "R" or "L" side of a patient, and other identification indicia. The invention provides a protective coating on its radiopaque parts to protect the user. The invention also contains glow-in-the-dark features to facilitate use in poorly lit areas.

II. Description of the Related Art

Any discussion of the prior art throughout the specification should in no way be considered as an admission that such prior art is widely known or forms part of common general knowledge in the field.

Medical instruments have been in use for years. Typically, medical instruments vary greatly in configuration depending on what procedure in which the medical instruments are utilized. One such procedure that medical instruments are utilized in are x-ray procedures.

During an x-ray procedure, x-ray markers are generally used to identify the left or right side of the anatomical part(s) of a patient, and other indicia taken during x-rays, such as the healthcare facility or the initials of an x-ray technician's name. The most common identification markers are the two-piece, left and right markers, which may include an x-ray technician's name or initials.

These small markers require the technician to keep track of two individual markers, even though only one marker may be required at a given time, and often result in the loss of one or both markers.

Additionally, the markers are frequently in use in dark areas and can be difficult for the technician to find or see during the procedure. Another issue is that image "artifacts" frequently show up on x-ray imaging, such as bullets, jewelry, surgical devices, and other items that are commonly mistaken for the x-ray marker.

In these respects, the x-ray markers according to the present invention substantially depart from the conventional concepts and designs of the prior art, and in doing so provide a single apparatus that is capable of marking either the "R" or "L" side of a patient and other identification indicia, glowing in the dark to facilitate use it low-light areas, and providing a radiopaque frame to eliminate the false identification of image artifacts as the x-ray marker.

BRIEF SUMMARY OF THE INVENTION

In view of the foregoing disadvantages inherent in the known types of medical instruments now present in the prior art, the present invention provides a new x-ray marker that is capable of marking either the "R" or "L" side of a patient and other identification indicia, glowing in the dark to facilitate use in low-light areas, and providing a radiopaque frame to eliminate the false identification of image artifacts as the x-ray marker.

The general purpose of the present invention, which will be described subsequently in greater detail, is to provide a new x-ray marker that has many of the advantages of the medical instruments mentioned heretofore and many novel features that result in a new x-ray marker which is not anticipated, rendered obvious, suggested, or even implied by any of the prior art medical instruments, either alone or in any combination thereof.

To attain this, the present invention generally comprises a base member containing a radiopaque frame and a radiopaque blocker shield that can be positioned over the "R" or "L" side of the base member to indicate the left or right side of a patient in x-ray procedures.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings.

The invention is capable of other embodiments and of being practiced and carried out in various ways. Also, it is to be understood that the phraseology and terminology employed herein are for the purpose of the description and should not be regarded as limiting.

A primary object of the present invention is to provide an x-ray marker that will overcome the shortcomings of the prior art devices.

A second object is to provide a single x-ray marker that is capable of indicating either the "R" or "L" side of a patient and other identification indicia.

Another object is to provide an x-ray marker that can be used in poorly lit areas.

An additional object is to provide an x-ray marker that eliminates the possibility of it being mistaken for image artifacts such as bullets, jewelry, surgical devices, and other items that are commonly mistaken for the marker.

A further object is to provide a single x-ray marker to prevent the x-ray technician from carrying two individual markers that are easily lost and misplaced.

Another object is to provide an x-ray marker that is compact, but provides clear and easy to read symbols on the x-ray image.

Another object is to provide an x-ray marker that can be easily cleaned and sanitized.

Another object is to provide a protective coating on the radiopaque material to protect the user during use of the device.

Another object is to provide several variations of the single x-ray marker that the x-ray technician can select from according to the technician's preference.

Another object is to provide a marker that can be efficiently and economically produced.

Other objects and advantages of the present invention will become obvious to the reader and it is intended that these objects and advantages are within the scope of the present invention.

To the accomplishment of the above and related objects, this invention may be embodied in the forms illustrated in the accompanying drawings, attention being called to the fact, however, that the drawings are illustrative only, and that changes may be made in the specific construction illustrated and described within the scope of the appended claims.

To accomplish the foregoing and other objects of this invention, there is provided a single identification marker. The device has a primary rectangular base made of radiotransparent and glow-in-the-dark material on which is located two cavities. One cavity contains a radiopaque "R," and the other cavity contains a radiopaque "L," which designate the left or right side of the anatomical part(s) of a patient being taken during an x-ray procedure. Each cavity is filled with a radiotransparent and glow-in-the-dark material to protect the user from the radiopaque "R" and "L" indicia during letter selection. The rectangular base also contains an embedded rectangular piece of radiopaque material that travels along the perimeter of the base to form a frame on the x-ray image around the indicia so that the x-ray technician can be sure that the technician is viewing the indicia on the film and not any image artifacts (such as bullets, surgical devices, jewelry, etc.).

A movable blocker shield made of radiopaque and glow-in-the-dark material covers either the "R" or "L" in one of three different embodiments: either as a swivel shield, as a hinge shield, or as a slider shield, thereby shielding one of the chosen symbols and causing the unshielded symbol to be marked on the x-ray image.

The blocker shield has a protective glow-in-the-dark coating to protect the user from the radiopaque material during letter selection.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 6 is a left side perspective view of FIG. 3.

FIG. 7 is a left side perspective view of FIG. 6 shown in an alternate position.

FIG. 8 is a left side perspective view of FIG. 6 shown in an alternate position.

FIG. 9 is a left side perspective view of FIG. 6 shown in an alternate position.

DETAILED DESCRIPTION OF THE INVENTION

A. Overview

Figure 1:
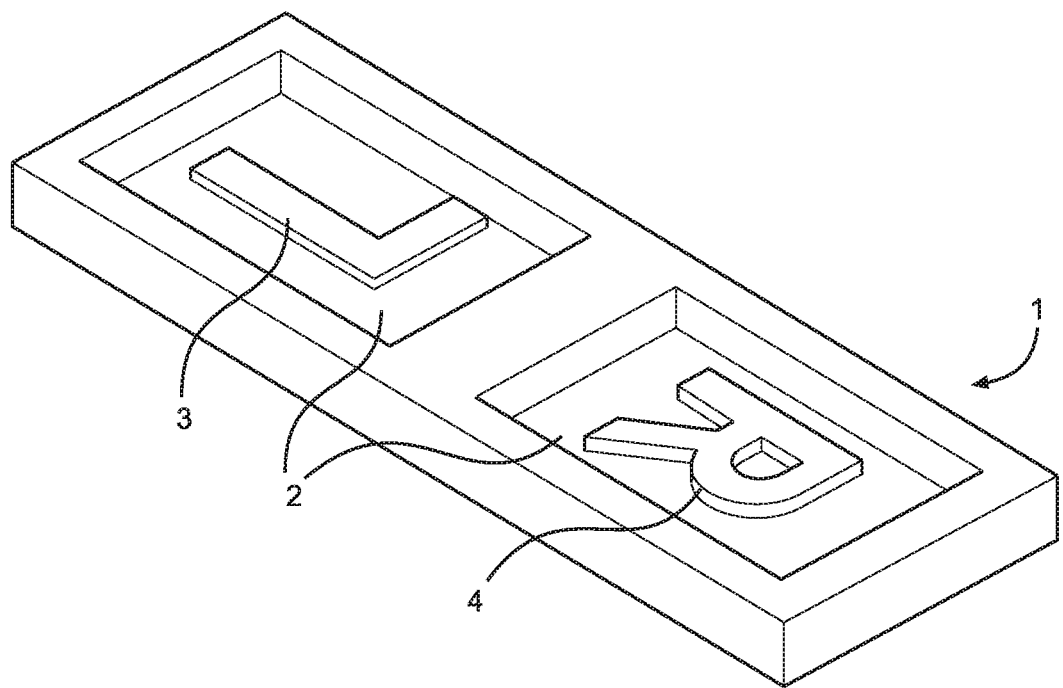
FIG. 1 is a left side perspective view of the base member.
Figure 2:
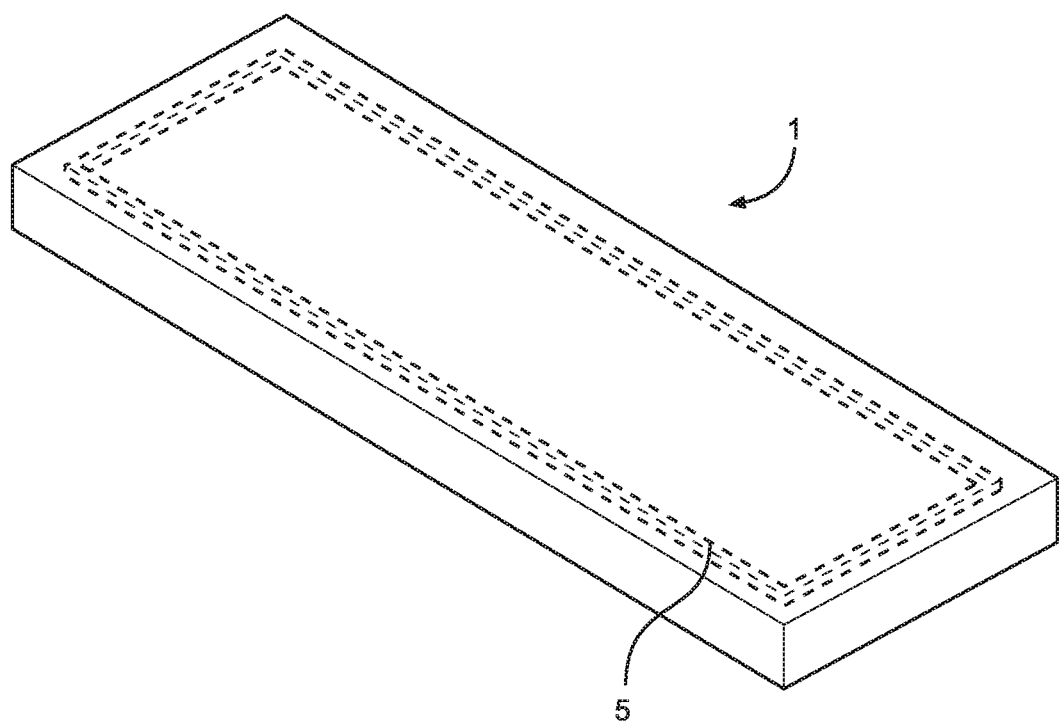
FIG. 2 is a rear perspective view of the base member.

Turning now descriptively to the drawings, in which similar reference characters denote similar elements throughout the several views, FIGS. 1 through 28 illustrate several embodiments of a single x-ray marker which is comprised of a base member 1 and blocker shield 9, 15, or 18.

B. Base Member

Though it can be used on its own, the base member 1 is preferably designed to be used with a blocker shield 9, 15, or 18. The base member 1 is also preferably comprised of a plastic glow-in-the-dark material; however other materials may be utilized in the construction of the base member 1, such as, but not limited to glow-in-the dark radiotransluent metal or other glow-in-the-dark radiotranslucent materials.

The base member 1 is preferably rectangular in nature and has two cavities 2 as shown in FIG. 1. In one cavity 2, is contained the radiopaque letter "L" 3, which is comprised of a radiopaque material such as lead, however, other radiopaque materials can be used. In the other cavity 2, is contained the letter "R" 4, which is also comprised of a radiopaque material such as lead, however, other radiopaque materials can be used. Each cavity 2, is filled with a radiotranslucent and glow-in-the-dark material such as clear plastic, which covers the radiopaque letters "L" 3 and "R"

4. Embedded within each base member 1 is a radiopaque frame 5 comprised of lead or other radiopaque materials.

Figure 3:
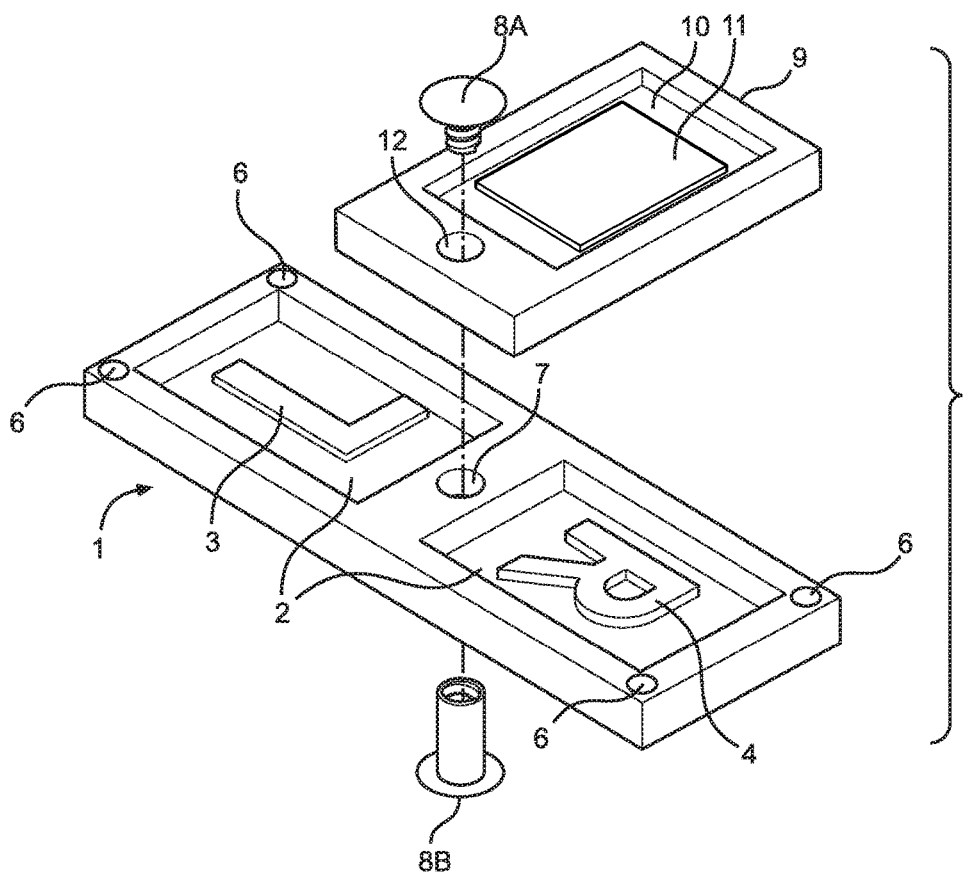
FIG. 3 is an exploded left side perspective view of one embodiment of the invention.
Figure 4:
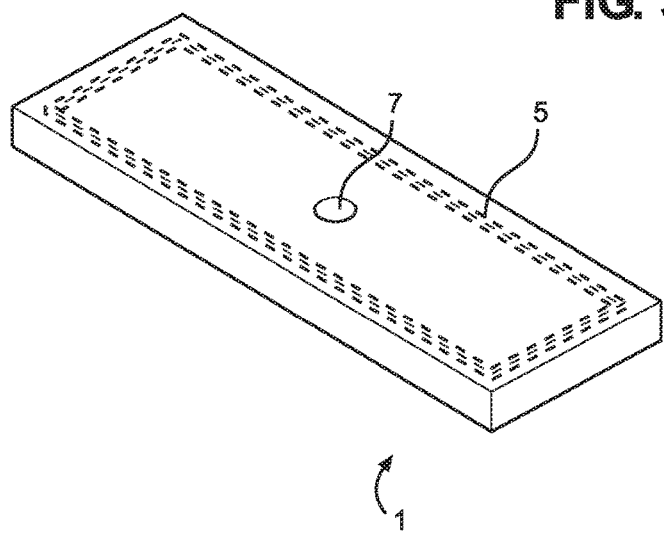
FIG. 4 is a rear perspective view of one embodiment of the base member.
Figure 5:
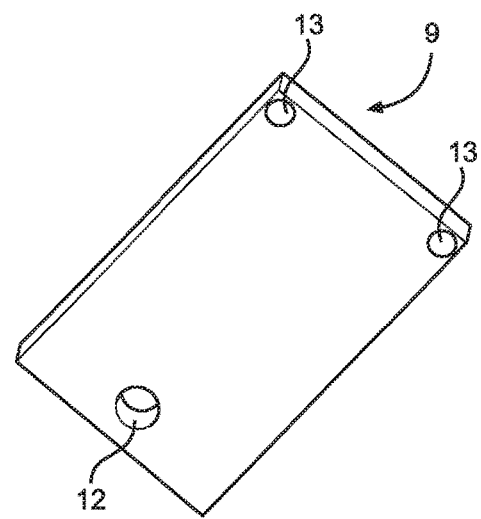
FIG. 5 is a rear perspective view of one embodiment of the blocker shield.
Figure 10:
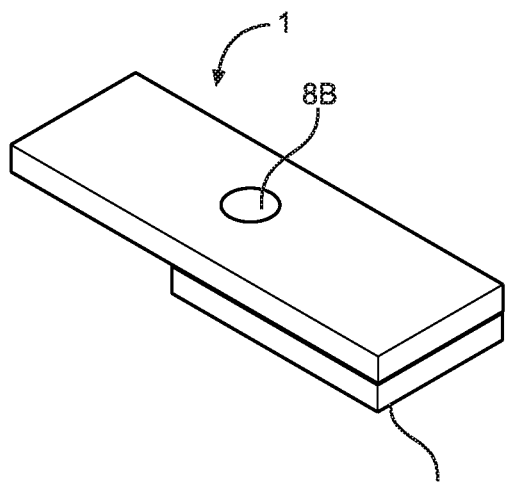
FIG. 10 is a rear perspective view of FIG. 6.
Figure 11:
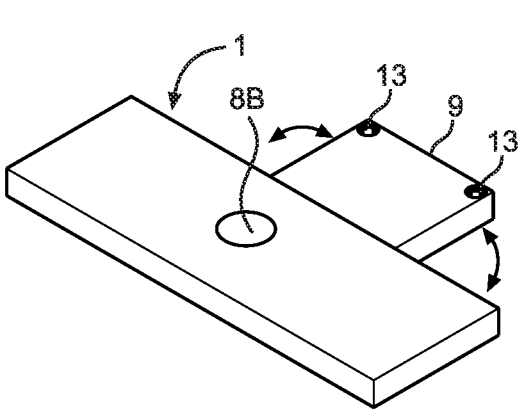
FIG. 11 is a rear perspective view of FIG. 10 shown in an alternate position.
Figure 12:
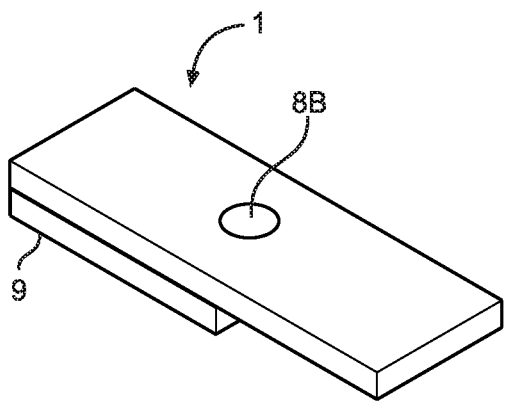
FIG. 12 is a rear perspective view of FIG. 10 shown in an alternate position.
Figure 13:
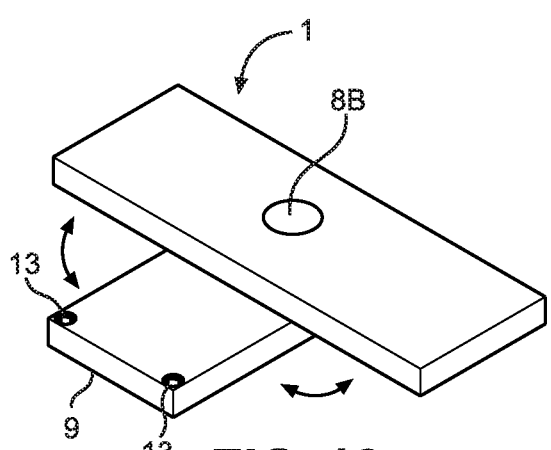
FIG. 13 is a rear perspective view of FIG. 10 shown in an alternate position.
Figure 14:
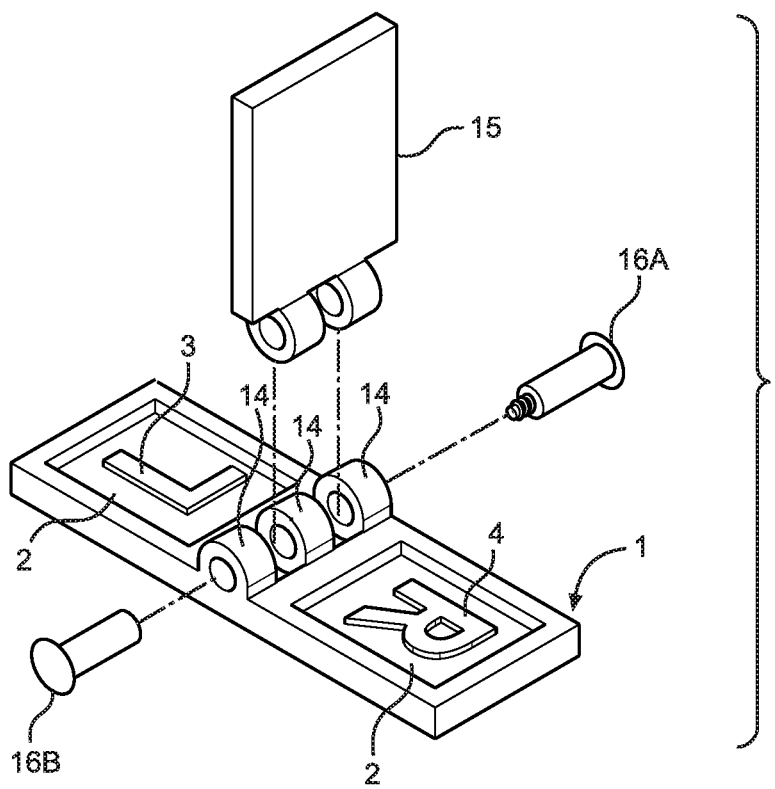
FIG. 14 is an exploded left perspective view of another embodiment of the invention.
Figure 15:
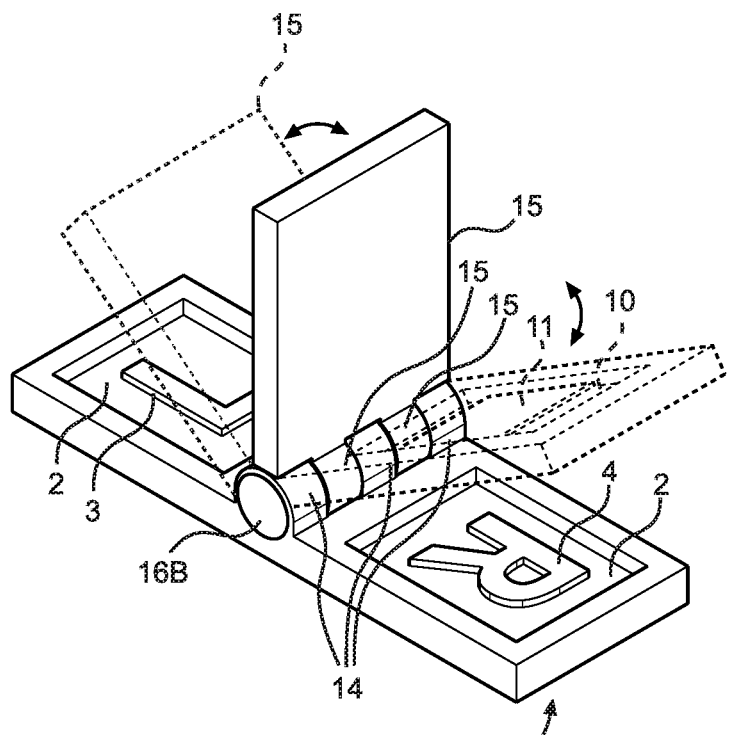
FIG. 15 is a left perspective view of FIG. 14 shown in alternate positions.
Figure 19:
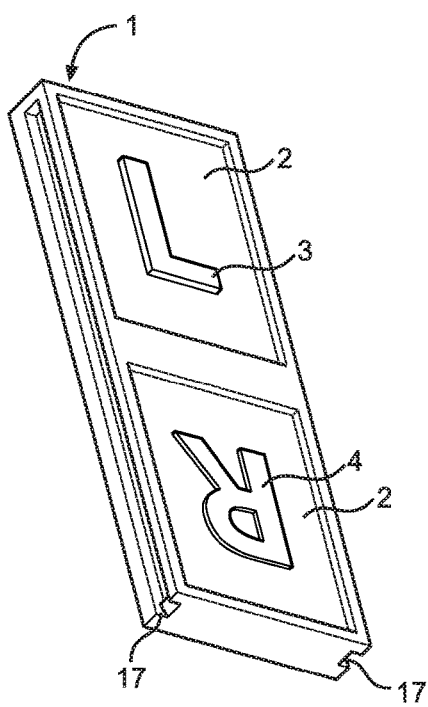
FIG. 19 is a left perspective view of another embodiment of the base member.

Another embodiment of base member 1, as shown in FIG. 4, has a hole 7 drilled into the center to permit a blocker shield 9 with a hole 12 to be attached to it using connectable screws 8A and 8B, as shown in FIG. 3. This embodiment also has four stoppers 6, preferably half-spherical in shape and made of a radiotranslucent material such as plastic or rubber, as shown in FIG. 3, which interact with holes 13, as shown in FIG. 5, to lock blocker shield 9 into an "L" or "R" position on base member 1. Another embodiment of base member 1, has three upraised loop tunnels 14 attached to it to allow a blocker shield 15 to be connected to it, using connectable screws 16A and 16B, as shown in FIG. 14. Another embodiment of base member 1, as shown in FIG. 19, has two sliding tunnels 17 drilled into it to permit a blocker shield 18 to be attached to it.

C. Blocker Shield

The blocker shield 9 is preferably rectangular in nature and preferably comprised of a plastic glow-in-the-dark material; however other materials may be utilized in the construction of the blocker shield 9, such as but not limited to glow-in-the-dark radiotranslucent metal or other glow-in-the-dark radiotranslucent materials. The lower frame of blocker shield 9 has a hole 12 drilled into it to allow it to connect with hole 7 of base member 1 using connectable screws 8A and 8B, as shown in FIG. 3. The upper frame of blocker shield 9 has one cavity 10 that contains a preferably rectangular radiopaque disk 11, as shown in FIG. 3. The cavity 10 is filled with a radiotranslucent and glow-in-the-dark material such as clear plastic, which covers the radiopaque disk 11. There are two partial holes 13 drilled into the upper back side of blocker shield 9, as shown in FIG. 5, which allow interaction with the stoppers 6, as shown in FIG. 3, to lock blocker shield 9 into an "L" or "R" position on base member 1.

Figure 16:
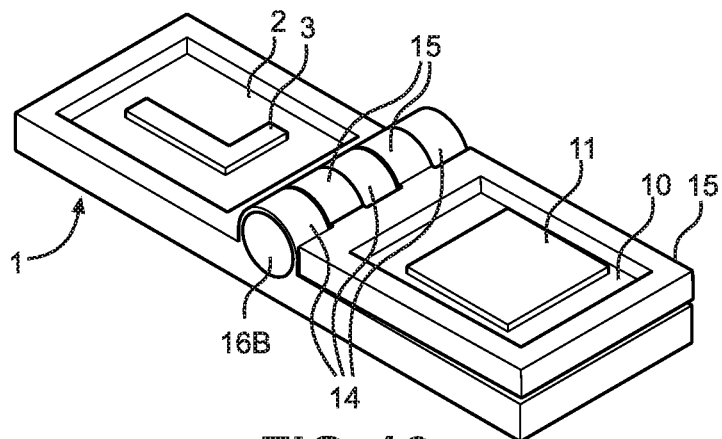
FIG. 16 is a left perspective view of FIG. 14 shown in an alternate position.
Figure 17:
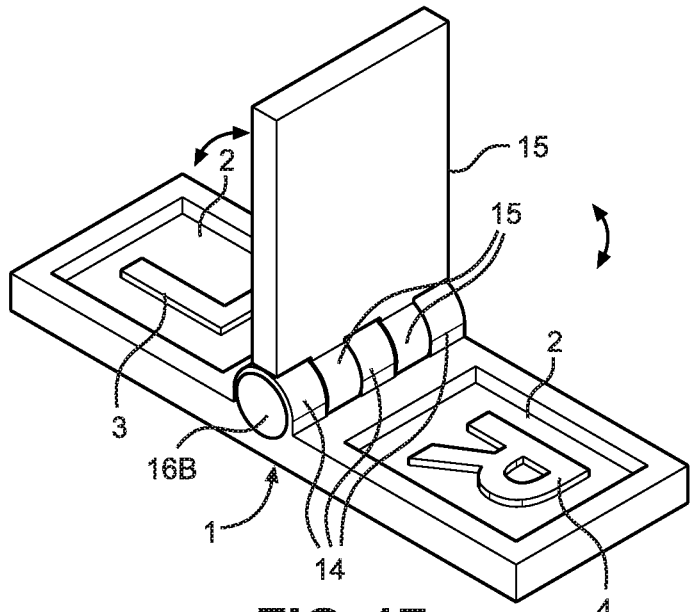
FIG. 17 is a left perspective view of FIG. 14 shown in an alternate position.
Figure 18:
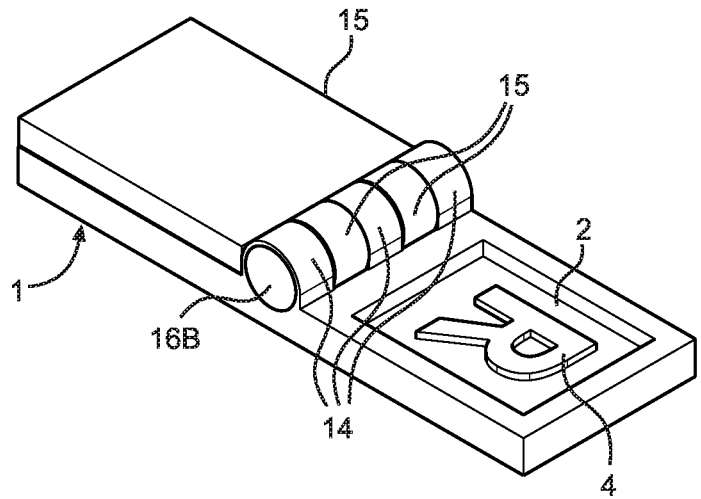
FIG. 18 is a left perspective view of FIG. 14 shown in an alternate position.

Another embodiment of blocker shield 9, is blocker shield 15, as shown in FIG. 14. Blocker shield 15 is preferably rectangular in nature and preferably comprised of a plastic glow-in-the-dark material; however other materials may be used in the construction of blocker shield 15, such as but not limited to glow-in-the-dark radiotranslucent metal or other radiotranslucent materials. The lower end of blocker shield 15 has two loop tunnels attached to it that allows it to interact with loop tunnels 14 of base member 1 using connectable screws 16A and 16B, as shown in FIG. 14. The front of blocker shield 15 contains a cavity 10 that contains a preferably rectangular radiopaque disk 11, as shown in FIG. 16. The cavity 10 is filled with a radiotranslucent and glow-in-the-dark material such as clear plastic, which covers the radiopaque disk 11.

Figure 20:
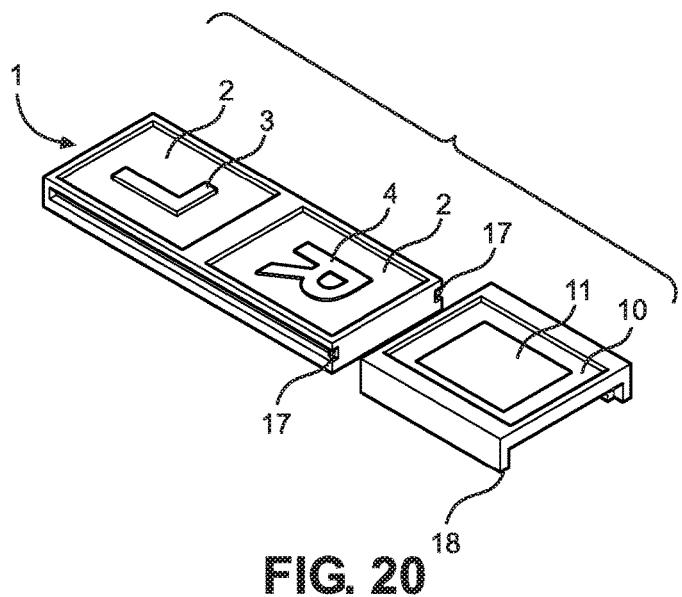
FIG. 20 is an exploded left perspective view of another embodiment of the invention.
Figure 21:
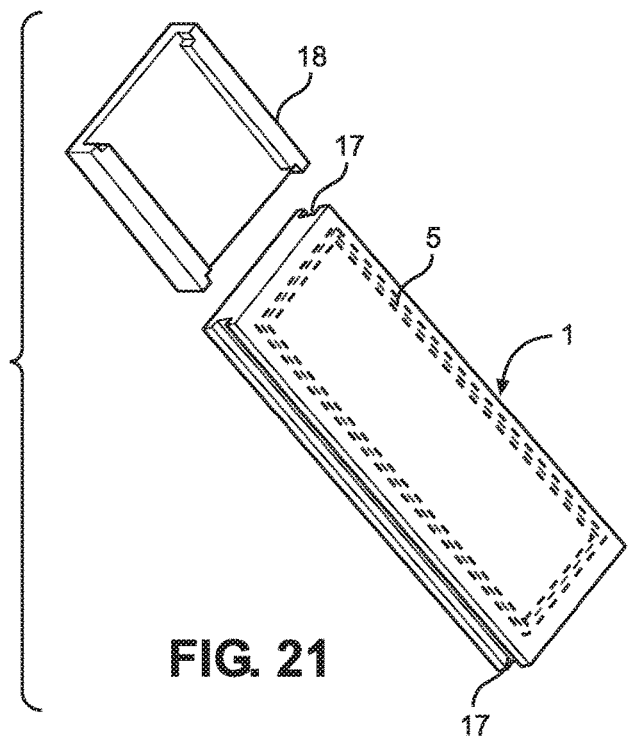
FIG. 21 is an exploded rear perspective view of FIG. 20.
Figure 22:
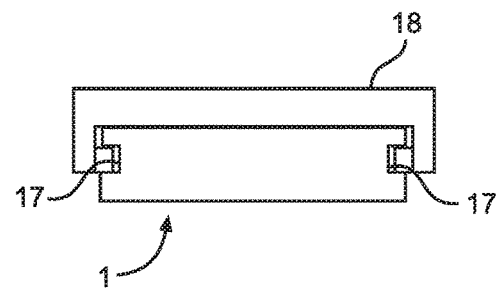
FIG. 22 is a bottom plan view of FIG. 20.
Figures 23, 24:
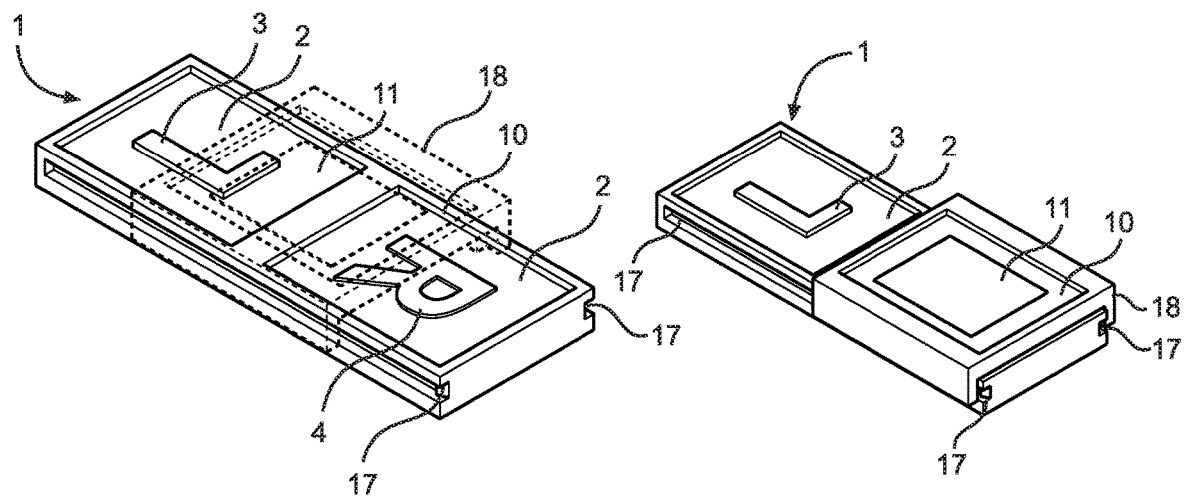
FIG. 23 is a left perspective view of FIG. 20 shown in alternate positions.
FIG. 24 is a left perspective view of FIG. 20 shown in an alternate position.
Figures 25, 26:
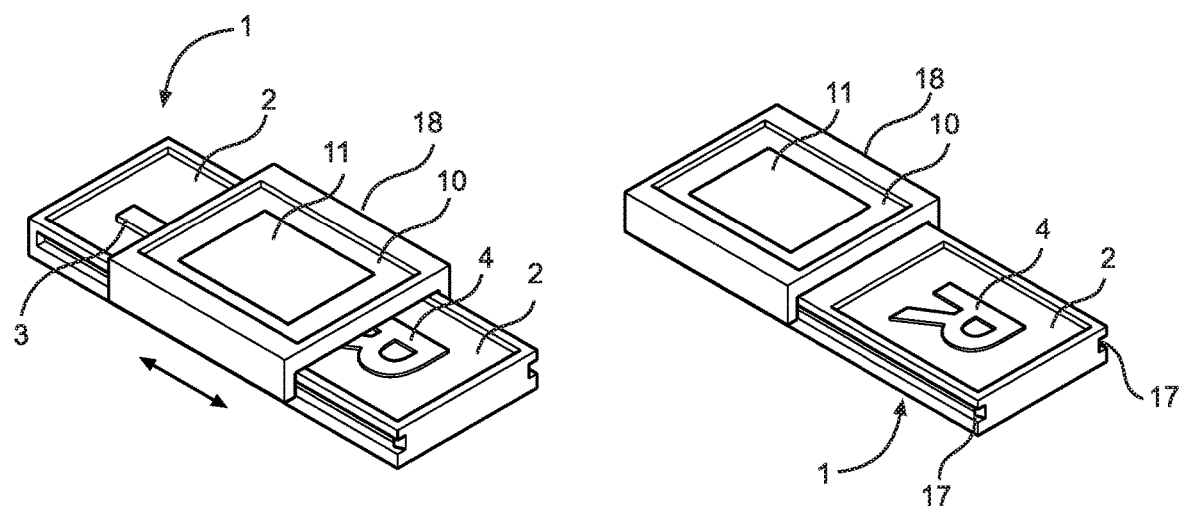
FIG. 25 is a left perspective view of FIG. 20 shown in an alternate position.
FIG. 26 is a left perspective view of FIG. 20 shown in an alternate position.

Another embodiment of blocker shield 9, is blocker shield 18, as shown in FIG. 20. Blocker shield 18 is preferably rectangular in nature and preferably comprised of a plastic glow-in-the-dark material; however other materials may be used in the construction of blocker shield 18, such as but not limited to glow-in-the-dark radiotranslucent metal or other radiotranslucent materials. The front side of blocker shield 18 contains a cavity 10 that contains a preferably rectangular radiopaque disk 11, as shown in FIG. 20. The cavity 10 is filled with a radiotranslucent and glow-in-the-dark material, such as clear plastic, which covers the radiopaque disk 11. The rear side of blocker shield 18 is hollow and contains two sliding channels that interact with sliding channels 17 on base member 1 as shown in FIGS. 21 and 22.

D. In Use

Figure 27:
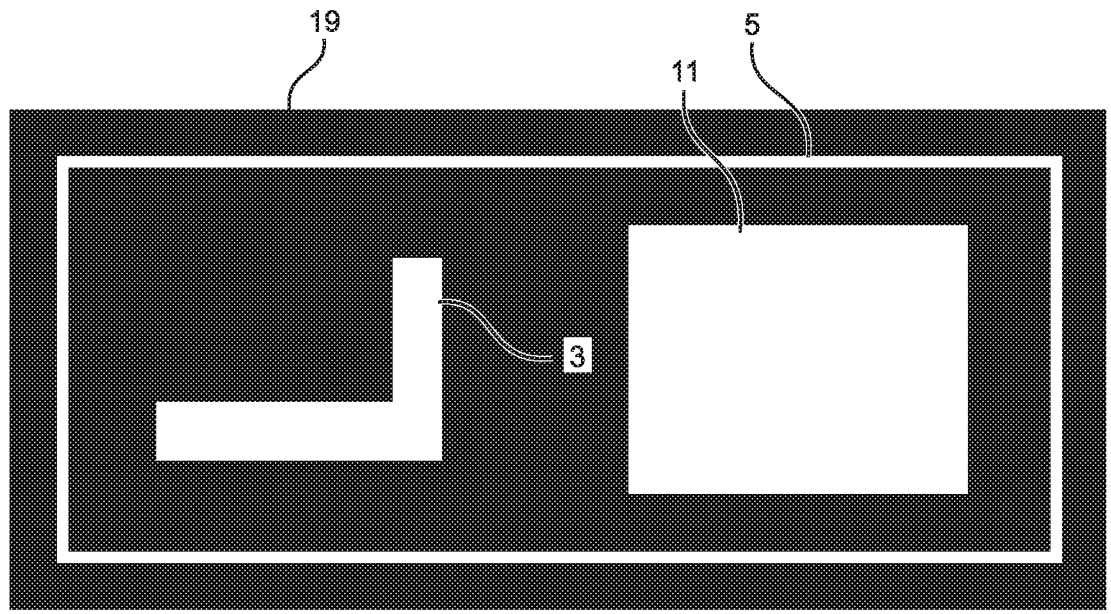
FIG. 27 is a front elevational view of the invention shown in use on x-ray imaging.
Figure 28:
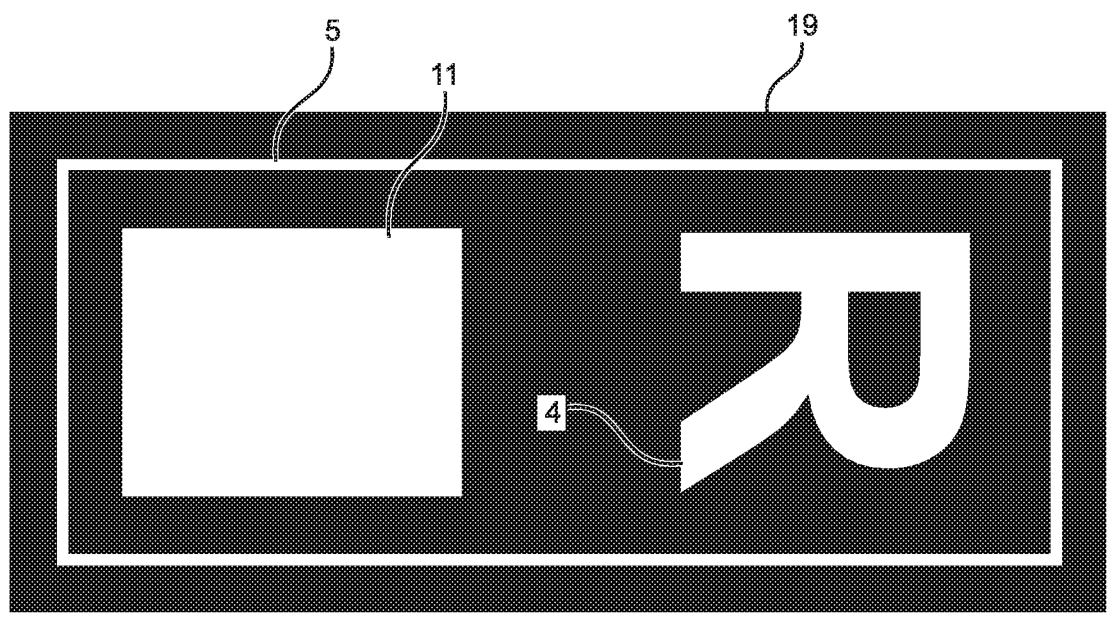
FIG. 28 is a front elevational view of FIG. 27 shown in an alternate position.

In use, the base member 1 with attached blocker shield 9, 15, or 18 is placed on the x-ray imaging cassette or digital receptor 19. The blocker shield 9, 15, or 18 is positioned over either the "L" 3 or "R" 4, depending on what side of the patient is being x-rayed. If the left side of the patient is being x-rayed, the blocker shield 9, 15, or 18 is positioned over the base member 1 so that it covers the "R" 4. Conversely, if the right side of the patient is being x-rayed, the blocker shield 9, 15, or 18 is positioned over base member 1 so that it covers the "L" 3. When the x-ray is completed, if the blocker shield 9, 15, or 18 was positioned over the "R" 4, then the radiopaque frame 5, radiopaque disk 11, and "L" 3 will appear on the x-ray image 19, as shown in FIG. 27. Conversely, when the x-ray is completed, if the blocker shield 9, 15, or 18 was positioned over the "L" 3, then the radiopaque frame 5, radiopaque disk 11, and "R" 4 will appear on the x-ray image 19, as shown in FIG. 28.

What has been described and illustrated herein are the preferred embodiments of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

We claim:

1. A single x-ray marker, comprising:
   a base member with an embedded radiopaque frame and two or more radiopaque indicia within the radiopaque frame; and
   a blocker shield containing radiopaque material for selectively blocking at least one of the two or more radiopaque indicia;
   wherein said two or more radiopaque indicia are covered with a chemical protective layer of radiotranslucent and glow in the dark material against the radiopaque material.

2. A single x-ray marker as in claim 1, wherein said two or more radiopaque indicia further comprise an "L" and an "R".

3. The single x-ray marker as in claim 1, wherein said base member is further comprised of radiotranslucent, glow in the dark material.

4. The single x-ray marker as in claim 1, wherein said base member further comprises two or more cavities for placement of said two or more radiopaque indicia and said two or more radiopaque indicia are filled with radiotranslucent and glow in the dark material to form the protective layer.

5. The single x-ray marker as in claim 1, wherein said blocker shield is further comprised of radio translucent, glow in the dark material.

6. The single x-ray marker as in claim 1, wherein the radiopaque material of said blocker shield is covered with a protective, radiotranslucent, and glow in the dark material.

7. The single x-ray marker as in claim 1, wherein said radiopaque frame is covered with a protective, radiotranslucent, and glow in the dark material.

8. A single x-ray marker, comprising:
   a base member with an embedded radiopaque frame and two or more radiopaque indicia within the radiopaque frame; and a blocker shield containing radiopaque material for selectively blocking at least one of the two or more radiopaque indicia;

wherein said two or more radiopaque indicia are covered with a chemical protective layer of radiotranslucent and glow in the dark material against the radiopaque material;

wherein said blocker shield has a lower opening and two partial holes drilled into the back of said blocker shield;

wherein said blocker shield is attached to said base member through said central opening using two connectable screws;

wherein said blocker shield is fully rotatable around said base member along the axes of said connectable screws; and wherein said blocker shield can be locked into position to select one of the two or more radiopaque indicia along the said base member through the interaction of said stoppers and said partial holes.

9. A single x-ray marker as in claim 8, wherein said two or more radiopaque indicia further comprise an "L" and an "R".

10. A single x-ray marker, comprising:

a base member with an embedded radiopaque frame and two or more radiopaque indicia within the radiopaque frame; and a blocker shield containing radiopaque material for selectively blocking at least one of the two or more radiopaque indicia;

wherein said two or more radiopaque indicia are covered with a chemical protective layer of radiotranslucent and glow in the dark material against the radiopaque material;

wherein said base member has three loop tunnels located on the face of said base member;

wherein said blocker shield has two loop tunnels attached to the bottom end of said blocker shield;

wherein said blocker shield is attached to said base member through said three loop tunnels using two connectable screws;

wherein said shield can hinge backwards and forwards along the axes of said two connectable screws; and wherein said blocker shield can be locked into either an "L" or an "R" position along the said base member through the hinging backwards and forwards of said blocker shield.

11. A single x-ray marker as in claim 10, wherein said two or more radiopaque indicia further comprise an "L" and an "R".

12. A single x-ray marker, comprising:

a base member with an embedded radiopaque frame and two or more radiopaque indicia within the radiopaque frame; and a blocker shield containing radiopaque material for selectively blocking at least one of the two or more radiopaque indicia;

wherein said two or more radiopaque indicia are covered with a chemical protective layer of radiotranslucent and glow in the dark material against the radiopaque material;

wherein said base member has a sliding channel drilled along each lateral side of said base member;

wherein said blocker shield has two sliding channels drilled inside the internal rear lateral sides of said blocker shield;

wherein said blocker shield is attached to said base member along said sliding channels drilled along each lateral side of said base member by sliding said blocker shield into said sliding channels of said base member along said blocker shield's said internal sliding channels; and wherein said blocker shield can be locked into position to block one of the two or more radiopaque indicia through sliding backward and forward of said blocker shield.

13. A single x-ray marker as in claim 12, wherein said two or more radiopaque indicia further comprise an "L" and an "R".

* * * * *